United States Patent [19]

Janmey et al.

[11] Patent Number: 5,783,662
[45] Date of Patent: Jul. 21, 1998

[54] POLYPHOSPHOINSITIDE BINDING PEPTIDES FOR INTRACELLULAR DRUG DELIVERY

[75] Inventors: Paul A. Janmey, Arlington; C. Casey Cunningham, Wayland; John H. Hartwig, Jamaica Plain; Thomas P. Stossel, Belmont, all of Mass.; Roland Vegner, Riga, Latvia

[73] Assignee: Brigham & Women's Hospital, Inc., Boston, Mass.

[21] Appl. No.: 843,035

[22] Filed: Apr. 11, 1997

Related U.S. Application Data

[63] Continuation of Ser. No. 394,027, Feb. 22, 1995, abandoned.
[51] Int. Cl.⁶ .............................. A61K 38/00; C07K 5/00; C07K 7/00
[52] U.S. Cl. .......................... 530/328; 530/345; 530/329; 530/330; 514/15; 514/16; 514/17
[58] Field of Search ..................................... 530/331, 330, 530/329, 328, 327, 345; 514/15

[56] References Cited

U.S. PATENT DOCUMENTS

| | | |
|---|---|---|
| 4,454,065 | 6/1984 | Gilvarg et al. |
| 4,861,581 | 8/1989 | Epstein et al. |
| 5,108,921 | 4/1992 | Low et al. |
| 5,164,315 | 11/1992 | Menez et al. |
| 5,245,551 | 9/1993 | Herron et al. ........................... 364/497 |
| 5,502,037 | 3/1996 | Kondratyev ............................... 514/21 |

FOREIGN PATENT DOCUMENTS

| | | |
|---|---|---|
| 0 347 526 | 12/1989 | European Pat. Off. |
| WO90/10448 | 9/1990 | WIPO |
| WO91/17170 | 11/1991 | WIPO |
| WO91/18981 | 12/1991 | WIPO |
| WO93/25564 | 12/1993 | WIPO |
| WO95/18221 | 7/1995 | WIPO |

OTHER PUBLICATIONS

Derossi, D. et al., The Third Helix of the Antennapedia Homeodomain Translocates through Biological Membrane, *J. of Biol. Chem.* 269:10444–10450, 1994.

Janmey, P. et al., Phosphoinositide-binding Peptides Derived from the Sequences of Gelsolin nad Villin, *J. of Biol. Chem.* 267:11818–11823, 1992.

LeRoux, I. et al., Neurotrophic activity of the Antennapedia homeodomain depends on its specific DNA-binding properties, *Proc.Natl.Acad.Sci. U.S.A.* 90:9120–9214 (1993).

Perez, F. et al., Antennapedia homeobox as a signal for the cellular internalization and nuclear addresing of a small exogeneous peptide, *J. of Cell Sci.* 102:717–722, 1992.

Molecular Probes, Inc. Handbook 1992–1994, Part IIB.5, pp. 20–41.

Reeck et al., "Homology" in Proteins and Nucleic Acids, 1987, Cell, 50.:667 (1987).

Yu et al., Identification of a Polyphosphoinositide–Binding Sequence in an Actin Monomer-Binding *J. Biol. Chem.* 267:14616–21 (1992).

Nakamura et al., Differential Expression of Bovine Adseverin in Adrenal Gland Revealed by in Situ Hybridization. *J. Biol. Chem.* 269:5890–96 (1994).

Bell et al., in Proteins and Enzymes. *Prentice Hall*, Englewood Cliffs, NJ, pp. 149–154 (1988).

Jablonski et al., Sugar Transport by the Bacterial Phosphotransferase System. *J. Biol. Chem.*, 258:9690–99 (1983).

Von Grunigen et al., Enzyme Immunoassay with Captured Hapten. *J. Biol.Chem.* Hoppe–Seyler, 372:163–172 (1991).

*Primary Examiner*—Avis M. Davenport
*Attorney, Agent, or Firm*—Wolf, Greenfield & Sacks, P.C.

[57] ABSTRACT

Methods and compositions for facilitating the transport of a membrane-impermeable extracellular agent having an intracellular activity across the membrane of a cell are provided. The methods involve covalently coupling an amino terminal blocking group to a transport-mediating peptide to form a carrier molecule. The carrier molecule is covalently coupled to the extracellular agent to form a membrane-permeable prodrug. The transport-mediating peptides are highly basic and bind to polyphosphoinositides.

13 Claims, 2 Drawing Sheets

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Phe  Lys  Ser  Gly  Leu  Lys  Tyr  Lys  Lys
    1                        5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

Gln  Arg  Leu  Phe  Gln  Val  Lys  Gly  Arg  Arg
    1                        5                        10

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

Lys  Tyr  Lys  Lys
    1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:4:

Leu  Lys  Tyr  Lys  Lys
    1                        5

( 2 ) INFORMATION FOR SEQ ID NO:5:

( i ) SEQUENCE CHARACTERISTICS:
        ( A ) LENGTH: 6 amino acids ( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:5:

Gly Leu Lys Tyr Lys Lys
1               5

( 2 ) INFORMATION FOR SEQ ID NO:6:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:6:

Ser Gly Leu Lys Tyr Lys Lys
1               5

( 2 ) INFORMATION FOR SEQ ID NO:7:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:7:

Lys Ser Gly Leu Lys Tyr Lys Lys
1               5

( 2 ) INFORMATION FOR SEQ ID NO:8:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:8:

Lys Gly Arg Arg
1

( 2 ) INFORMATION FOR SEQ ID NO:9:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:9:

Val Lys Gly Arg Arg
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

```
Gln Val Lys Gly Arg Arg
1               5
```

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
Phe Gln Val Lys Gly Arg Arg
1               5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Leu Phe Gln Val Lys Gly Arg Arg
1               5
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Arg Leu Phe Gln Val Lys Gly Arg Arg
1               5
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:14:

```
Lys  Ile  Leu  Leu  Lys  Gly  Lys  Lys
1                  5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:15:

```
Lys  Ile  Leu  Val  Lys  Asn  Lys  Lys
1                  5
```

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

```
Lys  Ile  Leu  Val  Lys  His  Lys  Lys
1                  5
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Gln  Arg  Leu  Leu  His  Val  Lys  Gly  Arg  Arg
1                  5                        10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:18:

```
Gln  Arg  Leu  Leu  His  Val  Lys  Gly  Lys  Arg
1                  5                        10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:19:

```
Gln Arg Leu Leu His Val Lys Gly Lys Lys
1               5                   10
```

( 2 ) INFORMATION FOR SEQ ID NO:20:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:20:

```
Thr Arg Leu Phe Gln Val Lys Gly Lys Arg
1               5                   10
```

( 2 ) INFORMATION FOR SEQ ID NO:21:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:21:

```
Pro Arg Leu Phe Gln Leu Tyr Ala Arg Arg
1               5                   10
```

( 2 ) INFORMATION FOR SEQ ID NO:22:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:22:

```
Lys Lys Leu Tyr Gln Val Lys Gly Lys Lys
1               5                   10
```

( 2 ) INFORMATION FOR SEQ ID NO:23:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:23:

```
Arg Lys Leu Tyr Gln Val Lys Gly Lys Lys
1               5                   10
```

( 2 ) INFORMATION FOR SEQ ID NO:24:

(i) SEQUENCE CHARACTERISTICS:
 (A) LENGTH: 3 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:24:

Phe Lys Ser
1

(2) INFORMATION FOR SEQ ID NO:25:

(i) SEQUENCE CHARACTERISTICS:
 (A) LENGTH: 4 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:25:

Phe Lys Ser Gly
1

(2) INFORMATION FOR SEQ ID NO:26:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:26:

Phe Lys Ser Gly Leu
1                 5

(2) INFORMATION FOR SEQ ID NO:27:

(i) SEQUENCE CHARACTERISTICS:
 (A) LENGTH: 6 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:27:

Phe Lys Ser Gly Leu Lys
1                 5

(2) INFORMATION FOR SEQ ID NO:28:

(i) SEQUENCE CHARACTERISTICS:
 (A) LENGTH: 7 amino acids
 (B) TYPE: amino acid
 (D) TOPOLOGY: linear (ii) MOLECULE TYPE: peptide (v) FRAGMENT TYPE: internal (xi) SEQUENCE DESCRIPTION: SEQ ID NO:28:

```
Phe  Lys  Ser  Gly  Leu  Lys  Tyr
1                    5
```

(2) INFORMATION FOR SEQ ID NO:29:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

```
Phe  Lys  Ser  Gly  Leu  Lys  Tyr  Lys
1                    5
```

(2) INFORMATION FOR SEQ ID NO:30:

(i) SEQUENCE CHARACTERISTICS:
        (A) LENGTH: 3 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

```
Gln  Arg  Leu
1
```

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

```
Gln  Arg  Leu  Phe
1
```

(2) INFORMATION FOR SEQ ID NO:32:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

```
Gln  Arg  Leu  Phe  Gln
1                    5
```

(2) INFORMATION FOR SEQ ID NO:33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

```
Gln Arg Leu Phe Gln Val
 1               5
```

(2) INFORMATION FOR SEQ ID NO:34:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

```
Gln Arg Leu Phe Gln Val Lys
 1               5
```

(2) INFORMATION FOR SEQ ID NO:35:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
Gln Arg Leu Phe Gln Val Lys Gly
 1               5
```

(2) INFORMATION FOR SEQ ID NO:36:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

```
Gln Arg Leu Phe Gln Val Lys Gly Arg
 1               5
```

POLYPHOSPHOINSITIDE BINDING PEPTIDES FOR INTRACELLULAR DRUG DELIVERY

This application is a continuation of application Ser. No. 08/394,027, filed Feb. 22, 1995 entitled POLYPHOSPHOINOSITIDE BINDING PEPTIDES FOR INTRACELLULAR DRUG DELIVERY and now abandoned.

GOVERNMENT SUPPORT

The invention described herein was supported in part by grants from the National Institutes of Health. The government has certain rights in this invention.

FIELD OF THE INVENTION

This invention relates to methods and compositions for facilitating the transport of a membrane-impermeable extracellular agent across a cell membrane. More particularly, the invention relates to covalent conjugates of N-terminal-blocked polyphosphoinositide (PPI) binding peptides and their use in pharmaceutical, diagnostic and genetic engineering applications.

BACKGROUND OF THE INVENTION

Transmembrane transport of membrane-impermeable molecules has long been recognized as an essential aspect of drug therapy and gene delivery into cells. The efficient transport of nucleic acids into cells is of particular importance for drug therapy involving the delivery of antisense oligonucleotides into cells to inhibit cellular or viral nucleic acid functions. In general, transport of nucleic acids into cells is an inefficient process because of the high charge density of nucleic acids which impedes transport across a hydrophobic membrane barrier. Thus, methods for delivering nucleic acids into cells have been limited to carrier molecules which can accommodate the particular size and charge characteristics of the nucleic acid, yet still be capable of transporting the nucleic acid across the cell membrane.

Physical methods for inserting nucleic acids into cells, e.g., microinjection, electroporation, osmotic shock, calcium-phosphate mediated transformation, scrape loading and rapid acceleration of DNA-coated, gold particles, are labor and time-intensive. Such methods frequently are cytotoxic and/or non-reproducible and are not easily adapted for in vivo drug therapy or even for large scale cell transformation in vitro. Biological methods for nucleic acid delivery into cells include liposome-mediated gene transfer (P. L. Felgner et al., Proc. Natl. Acad. Sci. U.S.A. 84:7413 (1987)), cell fusion, retroviral vectors (M. A. Eglitis et al. BioTechniques 6: 608 (1988), adenoviral vectors (K. L. Berkner, BioTechniques 6:616 (1988)) and receptor-mediated endocytosis. Conjugation of nucleic acids to membrane permeable peptides, as well as complexation of nucleic acids with sugar-lysine conjugates (G. Y. Wu and C. H. Wu, J.Biol.Chem. 263:14621 (1988)) or with positively charged lipids, e.g., N-1-(2,3-dioleyloxy)propyl]-N,N,N-trimethylammonium chloride, also have been reported to enhance transfection efficiency. However, none of these methods is without limitations.

In general, the delivery of an exogenous molecule into a cell via receptor-mediated endocytosis is a relatively slow process. Receptor-mediated delivery involves covalently coupling the exogenous molecule to a receptor-specific ligand to form a conjugate and allowing the conjugate to contact a (receptor-expressing) cell for a time sufficient to permit transmembrane transport of the conjugate. It is generally believed that binding of the ligand to the receptor in the cell membrane initiates movement of the receptor-ligand complex into the cell interior in the form of an endosome. Release of the contents of the endosome in the cell interior completes delivery of the exogenous agent to the intracellular matrix. Many receptor-mediated endocytotic systems have been characterized, including those recognizing biotin, galactose, mannose, transferrin, insulin, and peptide growth factors such as epidermal growth factor. See, e.g., U.S. Pat. No. 5,108,921, issued to Low et al., and EP 273,085 published Jul. 6, 1988. In addition to being relatively slow processes, such transport methods are limited in usefulness to cells which express the targeted surface receptor.

Polybasic polypeptides recently have been reported as carrier molecules for delivering exogenous agents into cells. Frankel and coworkers have reported that peptides derived from the TAT protein sequence (e.g., amino acids 37-72, 37-58 and 45-58) have been used to deliver several functionally intact proteins into various types of cells in culture (Proc. Natl. Acad. Sci. U.S.A. 91:664–668 (1994)). In general, TAT and the TAT-protein conjugates apparently entered the cells relatively slowly with efficient cell uptake requiring high levels of chloroquin. The requirement for a high chloroquin concentration for uptake of the TAT-protein conjugates suggests that the mechanism of TAT-mediated delivery involves receptor-mediated endocytosis since it is known that chloroquin prevents degradation of endocytosed proteins by interfering with vacuolar acidification.

Conjugates containing homeobox peptides derived from a DNA-binding region of a Drosophila homeobox protein also have been reported for transport of an exogenous protein across the membranes of cultured cells (Proc. Nat. Acad. Sci. U.S.A. 88:1864–1868 (1991); WO 91/18981, published Dec. 12, 1991). However, since the first data showing entry of the homeobox protein were obtained many minutes after addition to cells, we believe that the homeobox peptide conjugates entered the cells relatively slowly (on the order of hours).

In summary, although various physical and biological methods have been used to introduce membrane-impermeable exogenous molecules into cells, such methods have met with limited success. Many of the above-described methods are inefficient and have proven to be cytotoxic at therapeutic levels of the carrier molecule. None of the above-described methods disclose a carrier molecule for facilitating the transport of a membrane-impermeable molecule into a cell in a manner that is fast and efficient. In particular, none of the above-described methods disclose a carrier molecule for specifically targeting a lipid membrane component that is present in virtually all mammalian and vertebrate cells. Moreover, none of the above-described methods disclose delivering an exogenous agent to a fixed cell for subsequent analysis of one or more fixed cellular components. In view of the foregoing, there is still a need for improved methods and compositions for facilitating the delivery of membrane-impermeable biologically active molecules into cells. Such methods would permit the rapid transport of the membrane-impermeable molecules into a wide variety of cell types, regardless as to whether the cells have been subjected to prior fixation.

SUMMARY OF THE INVENTION

The present invention overcomes the problems of the prior art by providing a carrier molecule which rapidly and efficiently transports a membrane-impermeable extracellular molecule into a cell. Unlike the transport systems of the prior art, the carrier molecules of the present invention are effective at cold temperatures (e.g., about 4° C.), suggesting that the transport mechanism does not require receptor-mediated endocytosis or active cellular metabolism. As a result, the carrier molecules of the instant invention are useful for transporting extracellular agents across the membranes of intact, but chemically fixed (metabolically dead) cells.

Although applicants do not intend to limit the invention to a particular theory of transmembrane transport, it is believed that the carrier molecules of the invention are internalized in a mechanism which involves interaction of the peptide component of the carrier molecules with cell membrane polyphosphoinositide (PPI) molecules. PPI molecules are present in most, if not all mammalian and vertebrate cell membranes. Accordingly, the invention advantageously provides a method for delivering an extracellular molecule to virtually any type of mammalian or vertebrate cell without regard for the particular proteins expressed on the cell surface.

According to one aspect of the invention, a carrier molecule for facilitating the transport of a membrane-impermeable extracellular agent across the membrane of a cell is provided. The carrier molecule contains an amine derivatizing agent ("X") covalently coupled to the N-terminal (i.e., amino terminal) amine of a "transport-mediating peptide" ("P"). As used herein, "transport-mediating peptides" refers to peptides which, when covalently coupled to the extracellular agent in the form of a prodrug having the formula X-P-A, mediate transport of the extracellular agent across a cell membrane. The transport-mediating peptides of the invention are selected from the group consisting of Seq. I.D. No. 1, Seq. I.D. No. 2 and functionally equivalent peptides of Seq. I.D. Nos. 1 and 2. In a particularly preferred embodiment, the transport-mediating peptide is Seq. I.D. No. 1 (human gelsolin 135-142) or Seq. I.D. No. 2 (human gelsolin 160-169).

Functionally equivalent peptides of Seq. I.D. Nos. 1 or 2 refers to (1) fragments, (2) homologs and (3) analogs of Sequence I.D. Nos. 1 and 2, that can be used in accordance with the methods of the invention to transport an extracellular agent into a cell. Functionally equivalent peptides contain between three and ten amino acids and are capable of binding to a PPI (i.e., functionally equivalent peptides of Seq. I.D. Nos. 1 and 2 are PPI-binding peptides). Functionally equivalent peptides are identified in screening assays which detect the ability of a putative functionally equivalent peptide (in the form of the carrier molecule) to transport a membrane-impermeable extracellular agent into a cell. Such screening assays rely upon biochemical or physical measurements or functional activity tests to determine whether transport of the extracellular agent across the cell membrane has occurred.

The derivatizing agents that are useful for the purposes of the invention are identified in preliminary screening assays which measure the relative solubilities in a lipid layer of the putative derivatizing agent in coupled and uncoupled forms. The uncoupled derivatizing agent is significantly less soluble in the lipid layer compared to a derivatizing agent that is covalently coupled to a transport-mediating peptide. In a particularly preferred embodiment, the derivatizing agent is a fluorescent molecule, such as rhodamine or a rhodamine derivative. A derivatizing agent that is a fluorescent molecule is particularly useful because it permits detection of transmembrane transport of the carrier molecule or prodrug without requiring further modification of the carrier molecule or prodrug to contain detectable components.

The membrane-impermeable extracellular agent has an intracellular activity. As used herein, in reference to the extracellular agent, "membrane-impermeable" means that the extracellular agent (when not conjugated to the carrier molecule) cannot penetrate the cell membrane in sufficient amounts to effect its intracellular activity. Exemplary membrane-impermeable extracellular agents include peptides, proteins, oligonucleotides, antibiotics, antimicotics, anti-viral agents, anti-cancer agents, enzymes, enzyme modulators, and imaging agents. In the particularly preferred embodiments, the extracellular agent is an antibiotic, an oligonucleotide or a peptide.

The extracellular agent is covalently coupled to the carboxyl terminus of the transport-mediating peptide (in the form of the carrier molecule) to form a prodrug, having the formula X-P-A, which is transported across a cell membrane. In a preferred embodiment, the covalent bond between the extracellular agent and the transport-mediating peptide is a labile bond which is cleaved after the extracellular agent is delivered to the intracellular matrix, thereby releasing the extracellular agent in an underivatized form.

According to another aspect of the invention, cells containing the carrier molecule (X-P) and/or the prodrug (X-P-A) are provided. Exemplary cells to which the carrier molecules and/or prodrugs of the invention can be delivered include melanoma cells, fibroblast cells, neuronal cells, neutrophils, monocytes and blood platelets. Optionally, the cells can be fixed according to standard procedures and the carrier molecules of the invention can be used to facilitate delivery of the extracellular agent across the membranes of fixed cells.

According to yet other aspects of the invention, pharmaceutical compositions containing the above-described carrier molecules and prodrugs and methods for making the pharmaceutical compositions are provided. The methods involve preparing the carrier molecules or prodrugs of the invention and placing these compositions in a pharmaceutically acceptable carrier.

According to still another aspect of the invention, a method for facilitating the transport of a membrane-impermeable extracellular agent across the membrane of a cell is provided. The method involves contacting the cell with a prodrug containing the extracellular agent covalently coupled to the carrier molecule of the invention for a time sufficient to permit transport of the extracellular agent across the cell membrane. Preferably, the time sufficient for transport is on the order of five to thirty minutes. More preferably, the time for transport is on the order of 120 to 300 seconds, and most preferably, the time is on the order of 10 to 120 seconds. The method is useful for rapidly and efficiently facilitating the transport of an extracellular agent across a cell membrane in vitro (e.g., for delivering an oligonucleotide probe or primer to a fixed cell for in situ hybridization or for delivering an antibiotic to a bacterially-contaminated cell culture) or in vivo (e.g., for delivering an imaging agent to tumor cells in vivo).

These and other aspects of the invention as well as various advantages and utilities will be more apparent with reference to the detailed description of the preferred embodiments and in the accompanying drawings. All patents, patent publications and references identified in this document are incorporated in their entirety herein by reference.

DETAILED DESCRIPTION OF THE INVENTION

Figure 1A:
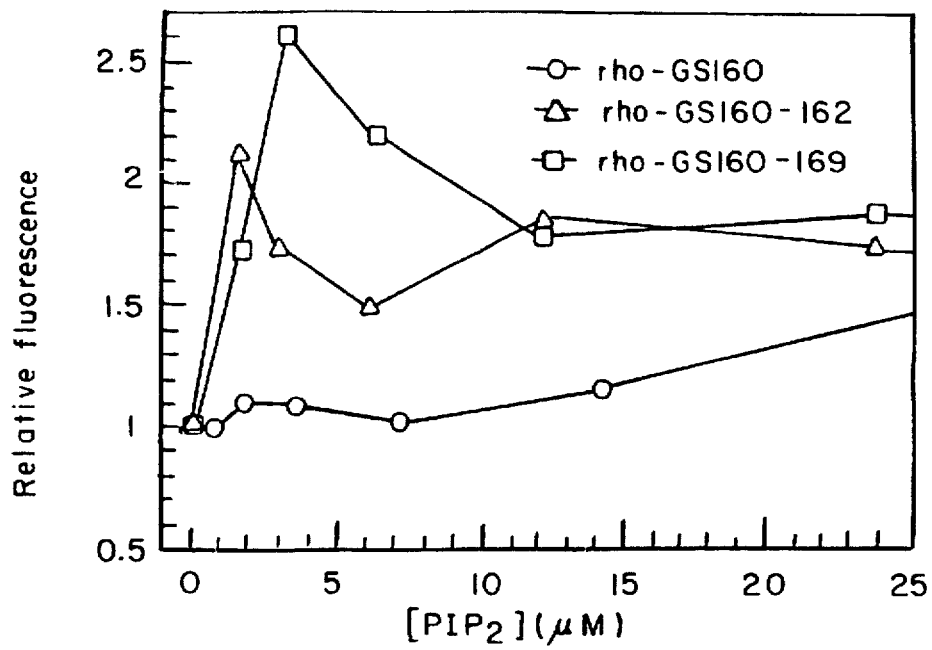
FIG. 1A shows the fluorescence intensity of 2 μM rhodamine-SEQ. I.D. No. 2 as a function of the concentration of phosphatidylinositol 4,5-bisphosphate (PIP2)

The instant invention embraces methods and compositions for facilitating the transport into a cell of a membrane-impermeable extracellular agent having an intracellular activity. According to one aspect of the invention, a carrier molecule for facilitating the transport of the extracellular agent, A, across a cell membrane is provided. The carrier molecule has the formula, X-P, wherein P is a transport-mediating peptide and X is an amine derivatizing agent that is covalently coupled to the amino terminal amine of the transport-mediating peptide. To facilitate transport of the extracellular agent into a cell, the extracellular agent is covalently coupled to the carboxyl terminus of the transport mediating peptide to form a prodrug having the formula X-P-A.

As used herein, "transport-mediating peptide" refers to a peptide which, when covalently coupled to the extracellular agent in the form of a prodrug, mediates transport of the extracellular agent across a cell membrane. A "transport-mediating peptide" is said to have a "transport-mediating activity", i.e., the ability to transport an extracellular agent across a cell membrane. The transport-mediating peptides of the invention include Sequence I.D. No. 1, functionally equivalent peptides of Sequence I.D. No. 1, Sequence I.D. No. 2, and functionally equivalent peptides of Sequence I.D. No. 2. Transport-mediating peptides which are functionally equivalent peptides of Sequence I.D. Nos. 1 and 2 are identified in screening assays which measure the ability of a carrier molecule (containing the putative transport-mediating functionally equivalent peptide) to mediate transport of an extracellular agent across a cell or other lipid bilayer membrane. An exemplary screening assay to identify transport-mediating peptides that are functional equivalents of Sequence I.D. Nos. 1 or 2 is described in Example 9.

As used herein, "functionally equivalent peptides" of Sequence I.D. Nos. 1 and 2 refers to (1) fragments, (2) homologs and (3) analogs of Sequence I.D. Nos. 1 and 2, that can be used in accordance with the methods of the invention to transport an extracellular agent across a cell membrane. Functionally equivalent fragments, homologs and analogs are described in detail below. In general, the functionally equivalent peptides contain between three and ten amino acids and are capable of binding to a polyphosphoinositide (PPI), i.e., functionally equivalent peptides of Sequence I.D. Nos. 1 and 2 are "PPI-binding peptides".

Fragments, homologs and analogs of Sequence I.D. Nos. 1 and 2 which are PPI-binding peptides are identified in one or more "screening assays". In general, such screening assays are of two types: (1) structural assays which detect formation of a complex containing the putative PPI-binding peptide in association with a PPI (e.g., assays which rely upon size separation such as centrifugation or gel filtration chromatography) and (2) functional assays which measure the ability of the peptide to bind to a PPI (e.g., by measuring the ability of the peptide to competitively inhibit binding between a PPI and a known PPI-binding peptide (such as Sequence I.D. No. 2) or to a known PPI-binding protein (such as human gelsolin)). See, e.g., Example 4 for an exemplary screening assay to identify a fragment of Sequence I.D. No. 2 that has the ability to bind to a PPI.

In a particularly preferred embodiment, the transport-mediating peptide is Sequence I.D. Nos. 1 or 2. These peptides have amino acid sequences which correspond to the amino acid sequences of portions of the PPI-binding domains of human gelsolin: the P1 domain (amino acids 135-142 (Sequence I.D. No. 1)) and the P2 domain (amino acids 161-169 (Sequence I.D. No. 2)) (Janmey, P. et al., J. Biol. Chem. 267:14616 (1992)).

The amino acid sequence of Seq. I.D. No. 1 contains the generic formula, KxxxKxKK, wherein K represents lysine (a basic amino acid) and x represents a neutral amino acid. The amino acid sequence of Seq. I.D. No. 2 contains the generic formula, RxxxxKxRR, wherein K represents lysine, R represents arginine (basic amino acids) and x represents a neutral amino acid. It is believed that the highly charged basic character of Sequence I.D. Nos. 1 and 2 plays an important role in the localization of the peptide to intracellular structures, e.g., nucleus.

As used herein, "fragments" of Sequence I.D. No. 1 refer to the peptides identified as Sequence I.D. Nos. 3 through 7 and Sequence I.D. Nos. 24 through 29. "Fragments" of Sequence I.D. No. 2 refer to the peptides identified as sequence I.D. Nos. 8 through 13 and 30 through 36. Fragments can be synthesized without undue experimentation using standard procedures known to those of ordinary skill in the art. Functionally equivalent peptide fragments of Seq. I.D. Nos. 1 and 2 are identified in screening assays which measure the ability of the peptide fragment, in the form of a prodrug, to mediate transport of an extracellular agent across a cell membrane. Each of Sequences 3 through 13 contains the highly basic four amino acid portion of Sequence I.D. Nos. 1 or 2 (see TABLES 1 and 2) that is believed to play an important role in PPI binding.

Accordingly, the invention is also useful for visualizing intracellular phosphoinositide structure, e.g., by using a biotinylated-peptide (e.g., SEQ. I.D. No. 2) to target the phosphoinositide, followed by contacting the labelled cell with gold-labelled avidin and visualizing the phosphoinositide structure by electron microscopy. Our observations that conjugates containing rhodamine covalently coupled to the N-terminus of one (Q), two (QR) or three (QRL) amino acids of Seq. I.D. No. 2 cannot penetrate neutrophil cell membranes are consistent with a hypothesis in which the basic carboxyl terminal amino acids play an important role in membrane transport in neutrophils. We have also observed that conjugates containing rhodamine covalently coupled to the N-terminus of the three amino acids (QRL) of sequence I.D. No.

TABLE 1

PEPTIDE FRAGMENTS OF SEQ.I.D. NO. 1
GELSOLIN DOMAIN I (gelsolin 135–142) KxxxKxKK

| Seq. I.D. No. 1 = FKSGLKYKK |
| Seq. I.D. No. 3 = KYKK |
| Seq. I.D. No. 4 = LKYKK |
| Seq. I.D. No. 5 = GLKYKK |
| Seg. I.D. No. 6 = SGLKYKK |
| Seq. I.D. No. 7 = KSGLKYKK |
| Seq. I.D. No. 24 = FKS |
| Seq. I.D. No. 25 = FKSG |

TABLE 1-continued

PEPTIDE FRAGMENTS OF SEQ.I.D. NO. 1
GELSOLIN DOMAIN I (gelsolin 135–142) KxxxKxKK

| | |
|---|---|
| Seq. I.D. No. 26 = | FKSGL |
| Seq. I.D. No. 27 = | FKSGLK |
| Seq. I.D. No. 28 = | FKSGLKY |
| Seq. I.D. No. 29 = | FKSGLKYK |

TABLE 2

PEPTIDE FRAGMENTS OF SEQ.I.D. NO. 2
P2 (gelsolin 161–169) RxxxxKxRR

| | |
|---|---|
| Seq. I.D. No. 2 = | QRLFQVKGRR |
| Seq. I.D. No. 8 = | KGRR |
| Seq. I.D. No. 9 = | VKGRR |
| Seq. I.D. No. 10 = | QVKGRR |
| Seq. I.D. No. 11 = | FQVKGRR |
| Seq. I.D. No. 12 = | LFQVKGRR |
| Seq. I.D. No. 13 = | RLFQVKGRR |
| Seq. I.D. No. 30 = | QRL |
| Seq. I.D. No. 31 = | QRLF |
| Seq. I.D. No. 32 = | QRLFQ |
| Seq. I.D. No. 33 = | QRLFQV |
| Seq. I.D. No. 34 = | QRLFQVK |
| Seq. I.D. No. 35 = | QRLFQVKG |
| Seq. I.D. No. 36 = | QRLFQVKGR |

2 weakly entered monocytes and exhibited some intracellular activity. Thus, it appears that conjugates can be prepared that are more efficient at transporting an extracellular agent into one particular cell type compared to another cell type, thereby permitting the enhanced delivery of the extracellular agent into a specific cell type contained in a diverse population of cell types.

The term "homolog" refers generally to a molecule which shares a common structural feature with the molecule to which it is deemed to be an homolog. As used herein, a "functionally equivalent peptide homolog" of Sequence I.D. Nos. 1 or 2, is a peptide which shares a common structural feature (amino acid sequence homology) and a common functional activity (transport-mediating activity) with Sequence I.D. Nos. 1 or 2. Functionally equivalent peptide homologs of Sequence I.D. Nos. 1 and 2 are derived from PPI-binding proteins that have sequence homology to human gelsolin.

For example, gelsolin is forty-five percent homologous with villin, a protein found in vertebrate brush border microvilli which, like gelsolin, exhibits Ca++ dependent actin severing activity. Gelsolin also is thirty-three percent homologous with severin and fragmin (P. Matsudaira and P. Janmey, Cell 54:139–140 (1988)). Other PIP-binding proteins having varying degrees of amino acid sequence homology to gelsolin include profilin, cofilin, Cap42(a), gCap39, CapZ, destrin, lipocortin (annexin) and DNase I. See, also WO 91/17170 and references identified therein. Additional proteins having sequence homology with gelsolin, and in particular, having sequence homology with the gelsolin PPI-binding domains, can be identified using art-recognized methods, e.g., searching data bases such as GENBANK for homologous peptides and/or proteins.

As used herein, a "functionally equivalent homolog" of Sequence I.D. Nos. 1 and 2 refers to a peptide (containing nine or ten amino acids, respectively) which shares at least 50% sequence homology with Sequence I.D. Nos. 1 or 2 (the common structural feature) and which has transport-mediating activity (the common functional activity). Exemplary functionally equivalent peptide homologs that have at least 50% sequence homology to Sequence I.D. Nos. 1 or 2 include, Sequence I.D. Nos. 14, 15, 16. Preferably, the peptide homologs have at least 60% sequence homology (e.g., Sequence I.D. Nos. 19 and 21) with Seq. I.D. Nos. 1 or 2, more preferably, at least 70% sequence homology (e.g., Sequence I.D. No. 18) and most preferably, at least 80% sequence homology (e.g., Sequence I.D. Nos. 17 and 20). See, e.g., Tables 3 and 4 for the preferred functionally equivalent peptide homologs of Sequence I.D. Nos. 1 and 2, respectively. In general, the functionally equivalent peptide homologs of Sequence I.D. No. 1 contain an amino acid substitution selected from the group consisting of S→I, G→L, Y→G, L→V and Y→H. The functionally equivalent peptide homologs of Seq. I.D. No. 2 contain an amino acid substitution selected from the group consisting of F→L, Q→H, R→K, Q→T, Q→P, V→L, K→Y, G→A, Q→K, F→Y and Q→R.

TABLE 3

TABLE OF PROTEINS HAVING SEQUENCE HOMOLOGY TO SEQ.ID No. 1 GELSOLIN DOMAIN I (gelsolin 135–142) KxxxKxKK Seq. 1 = FKSGLKYKK

| Sequence I.D. No. PPI-binding protein source | Sequence (amino acid substitution) |
|---|---|
| SEQ ID 14. phospholipase C-delta[1] 434–441 | KILLKGKK (S->I, G->L, Y->G) |
| SEQ ID 15. phospholipase C-beta[1] 451–458 | KILVKNKK (S->I, G->L, L->V, Y->G) |
| SEQ ID 16. phospholipase C-gamma[1] 458–465 | KILVKHKK (S->I, G->L, L->V, Y->H) |

[1]J.Biol.Chem. 267:14616 (1992)

TABLE 4

TABLE OF PROTEINS HAVING SEQUENCE HOMOLOGY TO SEQ.ID No. 2 GELSOLIN DOMAIN II (gelsolin 161–169) RxxxxKxRR Seq. 2 = QRLFQVKGRR

| Sequence I.D. No. PPI-binding protein source | Sequence (amino acid substitution) |
|---|---|
| SEQ ID 17. b-adseverin 138–147[1]: | QRLLHVKGRR (F->L, Q->H) |
| SEQ ID 18. h-villin 137–146: | QRLLHVKGKR (F->L, Q->H, R->K) |
| SEQ ID 19. c-villin 137–146: | QRLLHVKGKK (F->L, Q->H, R->K) |
| SEQ ID 20. d-gelsolin 184–193: | TRLFQVKGKR (Q->T, R->K) |
| SEQ ID 21. d-Quail 161–170[3]: | PRLFQLYARR (Q->P, V->L, K->Y, G->A) |
| SEQ ID 22. h-CapG 137–146[2]: | KKLYQVKGKK (Q->K, R->K, F->Y) |
| SEQ ID 23. m-CapG 138–147[2]: | RKLYQVKGKK (Q->R, R->K, F->Y) | where b is bovine, h is human, c is chicken, d is Drosophila.
[1]J.Biol.Chem. 269:5890 (1994)
[2]J.Biol.Chem. 267:16545 (1992)
[3]Cell 78:291 (1994)

As used herein, "functionally equivalent peptide analog" refers to functionally equivalent peptide fragments and homologs of Sequence I.D. Nos. 1 and 2 that contain conservative amino acid substitutions, provided that the peptide analogs which contain the conservative substitutions bind to a PPI and have transport-mediating activity, as determined, for example, in an in vitro screening assay (see, e.g., Example 8). As used herein, "conservative amino acid substitution" refers to an amino acid substitution which does not alter the relative charge or size characteristics of the peptide in which the amino acid substitution is made. Conservative substitutions of amino acids include substitutions made amongst amino acids within the following groups: (a) MILV; (b) FYW; (c) KRH; (d) AG; (e) ST; (f) QN; and (g) ED. In the particularly preferred embodiments, the functionally equivalent peptide analogs of Sequence I.D. Nos. 1 and 2 include at least one conservative amino acid substitution in which arginine and lysine are substituted for one another.

The derivatizing agent (X) is covalently coupled to the amino terminal primary amine of the transport-mediating peptide to form the carrier molecule (X-P). In general, the derivatizing agent is significantly less soluble in a lipid bilayer in an uncoupled form than when covalently coupled to the transport-mediating peptide in the form of the carrier molecule. Preferably, the derivatizing agent is a fluorescent molecule which can be easily detected using, for example, fluorescence microscopy. In the preferred embodiments, the derivatizing agent is rhodamine, a rhodamine-derivative, fluorescein, a fluorescein-derivative, biotin, or a biotin derivative. The derivatizing agent includes a reactive group that is capable of reacting with an amine to form a covalent bond. The preferred reactive group is a succinimidyl ester or an isothiocyanate. In a particularly preferred embodiment, the derivatizing agent is a positively charged fluorophore. Rhodamine and exemplary rhodamine derivatives are disclosed in ICN Biomedicals, Inc., 1994 Catalog, Costa Mesa, Calif.; Molecular Probes, 1992–1994 Catalog, Eugene, Oreg. and in TABLE 5. Fluorescein and exemplary fluorescein derivatives and structurally-related compounds are disclosed in the above-noted catalogs and in TABLE 6. In a particularly preferred embodiment, the derivatizing agent is rhodamine or a rhodamine derivative which includes a succinimidyl ester or an isothiocyanate reactive group. The derivatizing agents can be covalently coupled to the N-terminal amine group of the transport-mediating peptide using, for example, succinimide as described in the Examples. Exemplary amine-reactive derivatizing agents include fluorenylmethoxycarbonyl ("F-MOC").

TABLE 5

Rhodamine and Rhodamine-Derivatives rhodamine
rhodamine X isothiocyanate
tetramethylrhodamine-5-isothiocyanate
tetramethylrhodamine-6-isothiocyanate
4-carboxydihydrotetremethylrosamine, succinimidyl ester
4-carboxydihydro-X-rosamine, succinimidyl ester
6-carboxyrhodamine BG, hydrochloride
5-(and 6)-carboxyrhodamine B
5-(and 6)-carboxytetramethyl rhodamine
5-carboxytetramethylrhodamine, succinimidyl ester
5-(and 6)-carboxytetramethylrhodamine, succinimidyl ester
5-(and 6)-carboxy-X-rhodamine
5-(and 6)-carboxy-X-rhodamine, succinimidyl ester

TABLE 6

Fluorescein and Fluorescein-Derivatives fluorescein
fluorescein-5-isothiocyanate
fluorescein-5-isothiocyanate diacetate TABLE 6-continued Fluorescein and Fluorescein-Derivatives fluorescein-6-isothiocyanate
5-(and 6)-carboxy-2',7'-dichlorofluorescein diacetate, succinimidyl ester
5-(and 6)-carboxy-4',5'-dimethylfluorescein diacetate, succinimidyl ester
5-carboxyfluorescein, succinimidyl ester
5-(and 6)-carboxyfluorescein, succinimidyl ester
5-(and 6)-carboxyfluorescein diacetate, succinimidyl ester
5-(and 6)-carboxynaphthofluorescein
5-(and 6)-carboxynaphthofluorescein diacetate, succinimidyl ester
5-(and 6)-carboxynaphthofluorescein, succinimidyl ester
5-(3-carboxypropionyl)aminofluorescein (fluorescein succinamide)
2',7'-dichlorohydrofluorescein diacetate, succinimidyl ester
eosin-5-isothiocyanate
erythrosin-5-isothiocyanate
5-(and 6)-carboxyeosin
5-(and 6)-carboxyeosin diacetate, succinimidyl ester The transport properties of a preferred carrier molecule of the invention (the rhodamine-Sequence I.D. No. 2 conjugate) were discovered during experiments designed to elucidate the intracellular location and function of an isolated portion of the gelsolin P2 PPI-binding domain (Sequence I.D. No. 2). A rhodamine-peptide conjugate was prepared by coupling the N-hydroxysuccinimide ester of rhodamine B to the N-terminal amine group (glutamine) in Sequence I.D. No. 2. Because PPI-binding peptides are highly charged, such peptides are membrane-impermeable and must be microinjected to evaluate intracellular location and functional activities. The rhodamine-Sequence I.D. No. 2 conjugate initially was microinjected into human melanoma cells (Example 5). Surprisingly, the rhodamine-Sequence I.D. No. 2 conjugate entered human melanoma cells that had not been microinjected, i.e., cells that inadvertently had been exposed to conjugate contained in the extracellular culture medium.

Further experiments confirmed that placing the rhodamine-Sequence I.D. No. 2 conjugate in the extracellular medium of cultured human melanoma cells, resulted in rapid and efficient cellular uptake of the conjugate. Moreover, melanoma cells which had internalized the rhodamine-Sequence I.D. No. 2 conjugate displayed the same changes in cell morphology and function that were observed following microinjection of (uncoupled) Sequence I.D. No. 2.

Viewed by fluorescence microscopy, the rhodamine-Sequence I.D. No. 2 conjugate was observed to concentrate around the cell periphery at the plasma membrane, around the nuclear membrane, and especially in the nucleolus of human melanoma cells. A similar labeling pattern was observed in NIH-3T3 fibroblasts and neuronal cells with the growth cones of primary cultures of neurons also staining brightly. In addition to cultured human melanoma cells, NIH-3T3 fibroblasts and neuronal cells, the rhodamine-Sequence I.D. No. 2 conjugate was rapidly and efficiently internalized by chinese hamster fibroblasts and human blood platelets, human blood monocytes, polymorphonuclear leukocytes, dictyestelium discoidium. Regardless of the cell type, intracellular components were stained rapidly (i.e., on the order of seconds) following exposure to the conjugate (<about 10 uM) in the culture medium. That staining was not affected by exposure to cold temperatures (e.g., 4° C.) and entered into aldehyde fixed cells, suggests that the mechanism of transmembrane transport does not involve receptor-mediated endocytosis or require active cellular metabolism. Accordingly, the carrier molecules of the invention are useful for delivering membrane-impermeable extracellular agents across the membranes of cells which are incapable of undergoing endocytosis or active cellular metabolism (i.e., fixed cells).

Preliminary experiments also demonstrated that the preferred carrier molecule of the invention, rhodamine-Sequence I.D. No. 2, is not cytotoxic to human blood platelets at levels that were sufficient to mediate an intracellular functional activity. In particular, exposure of intact human blood platelets to 10 uM of the rhodamine-Sequence I.D. No. 2 conjugate in extracellular culture medium resulted in the rapid, efficient and complete blocking of thrombin and glass-induced platelet activation. No cytotoxic effects were observed at this concentration. These results suggest yet another utility for the carrier molecules of the invention, namely, preventing cold-induced platelet activation by binding to PPIs that are generated during platelet activation, thereby preventing the PPIs from interacting with endogenous actin filament capping proteins. Support for this hypothesis is found in experiments in which the introduction of the entire human gelsolin P2 PPI-binding domain (amino acids 150–169) into permeabilized human platelets, inhibited thrombin-induced actin assembly. This result suggests that the carrier molecules of the invention can be used to prevent cold-induced platelet activation by preventing actin filament severing. However, unlike the membrane-impermeable PPI-binding peptides of the prior art, the carrier molecules of the invention are rapidly taken up by human blood platelets, thereby simplifying the process for delivering the PPI-binding peptides across the membranes of platelets to prevent cold-induced platelet activation. See, e.g., WO 91/17170 and U.S. Pat. No. 5,358,844, issued to Stossel et al. for a discussion of the roles played by gelsolin in cold-induced platelet activation. By adjusting the amount of carrier molecule delivered to each platelet, a preparation of platelets can be prepared which will not undergo cold-induced platelet activation but which will retain the ability to respond to a stronger activating stimulus, such as thrombin. The amount of carrier molecule to achieve this objective is determined, for example, using the methods described in U.S. Pat. No. 5,358,844, e.g., by determining the minimal concentration of carrier molecule that can prevent cold-induced platelet activation yet permit thrombin-induced platelet activation (at physiologically relevant thrombin concentrations).

The carrier molecules of the invention are prepared by covalently coupling the derivatizing agent to the N-terminal amine group of the transport-mediating peptide. Derivatizing agents are selected which contain (or which can be modified to contain) a functional group that is reactive with the peptide N-terminal amine group (e.g., rhodamine succinate) and allowing the functional group and the peptide N-terminal amine to form a covalent linkage in accordance with art-recognized procedures. An exemplary procedure for forming the rhodamine-Sequence I.D. No. 2 carrier molecule is disclosed in Example 2. Other art-recognized methods for forming a covalent linkage can be used. See, e.g., March, J., *Advanced Organic Chemistry*, 4th Ed., New York, N.Y., Wiley and Sons, 1985), pp.326–1120.

In an analogous manner, the prodrugs of the invention can be prepared by covalently coupling an extracellular agent to a reactive group in the carboxyl terminus of the transport-mediating peptide. The extracellular agent has an intracellular function and is "membrane-impermeable". As used herein, "membrane-impermeable extracellular agent" refers to a molecule that is located in or introduced to the environment external to the cell, which molecule cannot penetrate the cell membrane at a sufficient level to mediate its intracellular function. Intracellular functions of the extracellular include, for example, an antibiotic function, an enzymatic function, and an oligonucleotide hybridizing function (e.g., for performing PCR amplification).

Exemplary extracellular agents include peptides, oligopeptides, proteins (e.g., apoproteins, glycoproteins, antigens and antibodies), haptens and antibodies thereto, receptors and other membrane proteins, protein analogs containing at least one non-peptide linkage in place of a peptide linkage, enzymes, enzyme modulators (e.g., coenzymes, inhibitors), amino acids and their derivatives, hormones, lipids, phospholipids, liposomes; toxins such as aflatoxin, digoxin, xanthotoxin, rubratoxin; antibiotics such as cephalosporins, penicillin, and erythromycin; analgesics such as aspirin, ibuprofen, and acetaminophen; bronchodilators such theophylline and albuterol; beta-blockers such as propranolol, metoprolol, atenolol, labetolol, timolol, penbutolol, and pindolol; antimicrobial agents further including ciprofloxacin, cinoxacin, and norfloxacin; antihypertensive agents such as clonidine, methyldopa, prazosin, verapamil, nifedipine, captopril, and enalapril; cardiovascular agents including antiarrhythmics, cardiac glycodides, antianginals and vasodilators; central nervous system agents including stimulants, psychotropics, antimanics, and depressants; antiviral agents; antihistamines such as chlorpheniramine and brompheniramine; cancer drugs including chemotherapeutic agents; tranquilizers such as diazepam, chordiazepoxide, oxazepam, alprazolam, and triazolam; anti-depressants such as fluoxetine, amitriptyline, nortriptyline, and imipramine; H-2 antagonists such as nizatidine, cimetidine, famotidine, and ranitidine; anticonvulsants; antinauseants; prostaglandins; muscle relaxants; anti-inflammatory substances; stimulants; decongestants; antiemetics; diuretics; antispasmodics; antiasthmatics; anti-Parkinson agents; expectorants; cough suppressants; mucolytics; vitamins; and mineral and nutritional additives. Extensive lists of these and other membrane-impermeable extracellular agents having an intracellular activity are provided in Remington's Pharmaceutical Science, 8th edition, ed. A. Gennaro, Mack Publishing Co., Easton, Pa. (1990) and in U.S. Pat. No. 5,108,921 issued to Low et al.

Other extracellular molecules having an intracellular activity that can be used in accordance with the invention include nucleotides; oligonucleotides; and their art-recognized and biologically functional analogs and derivatives including, for example, oligonucleotide analogs having phosphorothioate linkages; genes under the control of a promoter, plasmids, other nucleic acid vectors; antisense polynucleotides that can hybridize to an intracellular (cellular or viral) nucleic acid; promoters; enhancers; inhibitors; other ligands for regulating gene transcription and translation, and any other biologically active molecule that can be covalently attached to the carboxylate group of the above-described peptides without adversely affecting the ability of the peptide to bind to a PPI and transport the extracellular agent across a cell membrane.

Depending upon the nature of the reactive groups in the derivatizing agent, the peptide and the extracellular agent, the prodrug can be formed by simultaneously or sequentially allowing the functional groups of the above-described components to react with one another. Preferably, the transport-mediating peptide is prepared with a sulfhydryl group at, for example, the carboxyl terminus and then is coupled to the derivatizing agent to form the carrier molecule. Next, the carrier molecule is attached via its sulfhydryl group, to the membrane-impermeable extracellular agent. In an alternative preferred embodiment, the transport-mediated peptide extracellular agent complex is synthesized on a solid support and then this complex is attached to the derivatizing agent. In a preferred embodiment, the prodrug is formed by allowing the peptide to react with the derivatizing agent to form the carrier molecule X-P (see, e.g., Example 2), and then allowing the carrier molecule to react with the extracellular agent A to form the prodrug X-P-A (see, e.g., Example 7). An exemplary procedure for forming an antibiotic prodrug is shown in Example 10.

The extracellular agent contains a functional group that is reactive with a functional group in the carboxyl terminus of the transport-mediating peptide (e.g., the terminal carboxyl group). The prodrugs are formed by allowing the functional groups of the extracellular agent and the peptide to form a covalent linkage using coupling chemistries known to those of ordinary skill in the art. Numerous art-recognized methods for forming a covalent linkage can be used. See, e.g., March, J., *Advanced Organic Chemistry*, supra.

For extracellular agents which exhibit reduced intracellular activity in a conjugated form (e.g., an antisense oligonucleotide which exhibits reduced binding to a target nucleic acid when it is covalently attached to the carrier molecule), the covalent bond between the extracellular agent and the transport-mediating peptide is selected to be sufficiently labile (e.g., to enzymatic cleavage by an enzyme present in the cell) so that it is cleaved following transport of the extracellular agent into the cell, thereby releasing the free extracellular agent to the cell interior. Art-recognized biologically labile covalent linkages, e.g., imino bonds, and "active" esters can be used to form prodrugs where the covalently coupled extracellular agent is found to exhibit reduced intracellular activity in comparison to the intracellular activity of the extracellular agent alone. Exemplary labile linkages are described in U.S. Pat. No. 5,108,921, issued to Low et al.

If the polypeptide does not have a free amino- or carboxyl-terminal functional group that can participate in a coupling reaction, such a group can be introduced, e.g., by introducing a cysteine (containing a reactive thiol group) into the peptide by site directed mutagenesis. Disulfide linkages can be formed between thiol groups in, for example, the peptide and the extracellular agent. Alternatively, covalent linkages can be formed using bifunctional crosslinking agents, such as bismaleimidohexane (which contains thiol-reactive maleimide groups and which forms covalent bonds with free thiols). See also the Pierce Co. Immunotechnology Catalogue and Handbook Vol. 1 for a list of exemplary homo- and hetero-bifunctional crosslinking agents, thiol-containing amines and other molecules with reactive groups.

Other methods for covalently coupling the transport-mediating peptide to the derivatizing agent and/or to the extracellular agent include, for example, methods involving glutaraldehyde (M. Riechlin, Methods in Enzymology 70:159-165 (1980); N-ethyl-N'-(3-dimethylaminopropyl)-carbodiimide (T. L. Goodfriend et al., Science 144:1344-1346 (1964); and a mixture of N-ethyl-N'-(3-dimethylaminopropyl)-carbodiimide and a succinylated carrier (M. H. Klapper and I. M. Klotz, Methods in Enzymology 25:531-536 (1972)). In general, the carrier molecules and prodrugs of the invention can be prepared by using well-known methods for forming amide, ester or imino bonds between acid, aldehyde, hydroxy, amino, or hydrazo groups on the respective carrier molecule and prodrug components.

As would be apparent to one of ordinary skill in the art, reactive functional groups that are present in the amino acid side chains of the transport-mediating peptide (and possibly in the extracellular agent) preferably are protected, e.g., with protecting groups such as those shown in TABLE 7, to minimize unwanted side reactions prior to coupling the peptide to the derivatizing agent and/or to the extracellular agent. As used herein, "protecting group" refers to a molecule which is bound to a functional group and which may be selectively removed therefrom to expose the functional group in a reactive form. Preferably, the protecting groups are reversibly attached to the functional groups and can be removed therefrom using, for example, chemical or other cleavage methods. Thus, for example, the peptides of the invention can be synthesized using commercially available side-chain-blocked amino acids (e.g., FMOC-derivatized amino acids from Advanced Chemtech,Inc., Louisville, Ky.). Alternatively, the peptide side chains can be reacted with protecting groups after peptide synthesis, but prior to the covalent coupling reaction. In this manner, the carrier molecules and prodrugs of the invention can be prepared in which the amino acid side chain do not participate to any significant extent in the coupling reaction of the peptide to the derivatizing agent or to the extracellular agent.

TABLE 7

PROTECTING GROUPS THAT CAN BE CLEAVED FROM FUNCTIONAL GROUPS

Acid Sensitive protecting groups:

| Functional Group | Protecting Group |
| --- | --- |
| OH | t-Bu (tertiary butyl ether) |
| COOH | Ot-Bu (tertiary butyl ester) |
| NH2 | BOC (tertiary butyloxycarbonyl) |
| Guanidine | MTR (4-Methoxy-2,3,6-trimethyl-benzene-sulfonyl) or PMC (2,2,5,7,8-Pentamethychroman-6-sulfonyl) |
| Histidine | Trt (Triphenylmethyl) |
| SH | Trt (Triphenylmethyl) |

Base Sensitive protecting groups:

| Functional Group | Protecting Group |
| --- | --- |
| NH2 | FMOC (fluorenylmethoxycarbonyl |

The mechanism for carrier-mediated transport in accordance with the methods of the invention has not been completely elucidated. It is believed that blocking the N-terminal amine of Sequence I.D. No. 2 (a glutamine residue) and/or covalently attaching a cyclic molecule in the vicinity of the glutamine residue confers upon the peptide the ability to penetrate a cell membrane. Simply attaching rhodamine, fluorescein or pyrene upstream of the glutamine residue (e.g., attaching these molecules via a cysteine residue to the amino terminus of a peptide containing the entire human gelsolin P2 PPI-binding domain (amino acids 150-169) does not result in a transport-mediating peptide. Such conjugates (e.g., pyrene-Cys-P2 domain, rhodamine-B-Cys-P2 domain, and fluorescein-Cys-P2 domain) did not enter intact human blood platelets, NIH-3T3 fibroblasts or melanoma cells (as determined by functional activity assays).

In contrast to the above-described conjugates, the rhodamine-Sequence I.D. No. 2 conjugate was rapidly and efficiently taken up by the above-identified cells (as determined using fluorescence measurements and functional assays). For example, at concentrations significantly less than 5 uM, the rhodamine-Sequence I.D. No. 2 conjugate resulted in punctate staining of melanoma cells without altering the surface protrusion activity of these cells, indicating that the conjugate was not cytotoxic at these concentrations. That contacting the cells with the rhodamine-Sequence I.D. No. 2 conjugate did not result in uptake of free fluorescein or induce a large increase in intracellular free calcium suggests that the mechanism by which the conjugate mediates transmembrane transport does not involve merely permeabilizing the cell membrane. Moreover, that the membrane transport-mediating properties of the rhodamine-Sequence I.D. No. 2 conjugate were manifest in the presence of serum (which contains lipids) but were blocked if the carrier molecule was first contacted with micelles of phosphatidylinositol-4,5-bisphosphate strongly suggests that the carrier molecules of the invention mediate transmembrane transport by binding to membrane PPIs. Thus, although the exact mechanism of transmembrane transport has not been determined, our observations are consistent with a mechanism in which the carrier molecules and prodrugs of the invention form micelles prior to binding to membrane PPIs and that the exogenous agents are transported across the cell membrane in the form of micelles.

The invention also provides a method for facilitating the transport of a membrane-impermeable extracellular agent across the membrane of a cell. The method involves contacting the cell with the extracellular agent covalently coupled to the above-described carrier molecule of the invention, for a time sufficient to permit transport of the extracellular agent across the cell membrane. The time sufficient for transport is determined using routine optimization. In general, the time sufficient for transport is on the order of 10 to 300 seconds. Preferably, the derivatizing agent is a fluorescent molecule (e.g., rhodamine or fluorescein) and the transport-mediating peptide is selected from the group consisting of Sequence I.D. Nos. 1–36. In a most preferred embodiment, the carrier molecule contains rhodamine covalently coupled to Sequence I.D. Nos. 1 or 2.

The carrier molecules of the invention are particularly useful for delivering an extracellular agent to cells in vitro. Exemplary procedures for delivering an extracellular agent that is an antibiotic or an oligonucleotide to cells in vitro are provided in Examples 10 and 11, respectively. In general, the methods of the invention for delivering the extracellular agent to cells in vitro utilize art-recognized protocols with the only substantial procedural modification being the substitution of the prodrug for the drug used in the art-recognized protocol.

According to another aspect of the invention, the extracellular agent is an antibiotic and the invention is used to deliver the antibiotic to the cytoplasm of cells in vivo or in vitro. Bacterial contamination of cells in culture is frequently associated with large scale production of recombinant molecules. Unfortunately, although contaminated cultures can be treated with relatively large doses of antibiotic, such treatment is ineffective at eliminating bacteria which reside within the cells, i.e., the antibiotics do not efficiently enter the contaminated cells to destroy intracellular bacteria. The invention overcomes this problem by providing a carrier molecule for delivering the antibiotic to the cell cytoplasm, thereby eliminating intracellular bacterial contamination. Thus, the methods of the invention for reducing bacterial contamination of cells in culture are identical to methods that use conventional antibiotic treatment with the exception that the antibiotic prodrug is substituted for the conventional antibiotic drug in the standard procedure.

According to another embodiment, the extracellular agent is an oligonucleotide and the carrier molecule of the invention is used to deliver the oligonucleotide to the cell to effect in vitro or in vivo cellular transformation. According to yet another embodiment, the extracellular agent is an antisense RNA that is capable of hybridizing to a target intracellular nucleic acid (e.g., a cell or viral nucleic acid) and the carrier molecules of the invention are used to deliver the antisense RNA into the cell to modulate transcription of the target intracellular nucleic acid in vitro or in vivo.

In accordance with yet another embodiment of the invention, the extracellular agent is an oligonucleotide probe or primer and the carrier molecules of the invention are used to deliver the oligonucleotide probe or primer to the cell for in situ hybridization to a target nucleic acid and subsequent amplification using, for example, the polymerase chain reaction (PCR). See e.g., U.S. Pat. No. 4,683,202, issued to Mullis and Example 11. In situ hybridization coupled with PCR amplification is useful for detecting a variety of cellular and non-cellular (e.g., viral) nucleic acids. According to this embodiment, the method for in situ PCR involves transporting the oligonucleotide primer in the form of a prodrug into the cell, allowing the oligonucleotide primer to hybridize to an intracellular target nucleic acid, amplifying the target nucleic acid in situ and detecting the amplified target nucleic acid. The extracellular agent (such as a DNA probe) can be delivered to fixed or unfixed intact cells for performing PCR amplification and detecting intracellular nucleic acids.

According to another aspect of the invention, the carrier molecules are used for delivering an extracellular agent to cells in vivo. According to this aspect of the invention, the prodrugs of the invention are placed in a pharmaceutically acceptable carrier and are delivered to a mammalian recipient in accordance with known methods of drug delivery. Exemplary procedures for delivering an extracellular agent that is an imaging agent or a therapeutic agent are provided in Examples 12 and 13, respectively. The preferred imaging agents and therapeutic agents for use in accordance with the method of the invention include those disclosed in U.S. Pat. No. 4,861,581, issued to Epstein et al. (see Example 12). In general, the methods of the invention for delivering the extracellular agent in vivo utilize art-recognized protocols for delivering the agent with the only substantial procedural modification being the substitution of the prodrug for the drug used in the art-recognized protocol.

According to yet another aspect of the invention, a method for manufacturing a pharmaceutical composition for delivering a carrier molecule or extracellular agent having an intracellular activity to a cell in vivo is provided. The method involves placing the above-described carrier molecule or prodrug in a pharmaceutically acceptable carrier to form a pharmaceutical composition and administering the pharmaceutical composition containing a therapeutically effective amount of the prodrug to the recipient.

In general, a therapeutically effective amount of carrier molecule or prodrug is between about 1 ug and about 100 mg/kg. The carrier molecule or prodrug may be used alone or in appropriate association, as well as in combination with other pharmaceutically active compounds. The carrier molecule or prodrug may be formulated into preparations in solid, semisolid, liquid or gaseous form such as tablets, capsules, powders, granules, ointments, solutions, suppositories, and injections, in usual ways for oral, parenteral, or surgical administration. For topical applications, the carrier molecule or prodrug of the invention can be formulated as ointments or creams. Exemplary pharmaceutically acceptable carriers for peptide drugs, described in U.S. Pat. No. 5,211,657, are useful for containing the carrier molecules and prodrugs of the invention.

According to another aspect of the invention, the carrier molecules of the invention are useful as agents for modulating PPI-mediated signal transduction. Unlike the isolated (membrane-impermeable) PPI-binding peptides of the prior art, the PPI-binding peptides of the instant invention are presented in a membrane permeable form (e.g., covalently coupled to rhodamine or a rhodamine derivative), thereby eliminating the necessity for, e.g., microinjection or liposome encapsulation, to deliver the PPI-binding peptide to the cell interior in order to mediate signal transduction. Thus, the invention advantageously provides PPI-binding peptides in the form of carrier molecules that can be administered in accordance with art-recognized methods for drug delivery in vivo.

The carrier molecules can be formulated into a topical pharmaceutic preparation to deliver to local cells an amount of PPI-binding peptide sufficient to inhibit PPI-related signal transduction pathways such as those involved in cell trafficking and proliferation. For example, the topical application to the skin of a PPI-binding peptide in the form of a carrier molecule is useful for inhibiting cell proliferation associated with conditions such as psoriasis. Topical application of the carrier molecules of the invention by catheter to an arterial wall is useful for preventing post-angioplasty thrombosis or restenosis.

EXAMPLES

The instant invention provides methods and compositions for facilitating the transport of an exogenous agent across a cell membrane. The following examples illustrate representative utilities of the instant invention.

Example 1

Peptide Synthesis Procedure

A standard solid-phase synthesis procedure was used for making the peptides, namely the Fmoc/t-Bu protection procedure was used with carbodiimide and N-hydroxybenzotriazole coupling, beaded Wang resin, trifluoroacetic acid deprotection and HPLC reverse phase (RP) purification as described in, for example, E. Atherton and R. C. Sheppard, "Solid Phase Peptide Synthesis-A Practical Approach" IRL Press, 1989, Chapters 2, 5, 11.

Example 2

Procedure for Synthesizing X-P

A standard active ester coupling procedure is used to synthesize X-P. The rhodamine B N-hydroxysuccinimide is coupled with the N-terminal amino group of the peptide. The reaction is carried out in dimethylformamide at room temperature for several hours. See, e.g., Molecular Probes Handbook 1992–1994, Part IIB.5 for a list of exemplary references describing reactions of rhodamine "succinimidyl esters."

The rhodamine used in the working Examples was prepared from rhodamine B and N-hydroxysuccinimide by a standard dicyclohexylcarbodiimide coupling procedure (the ratio of reactants was 1:1.2:1.2 in $CH_2Cl_2$, 1 h at 0° C., then 20 h at 20° C.; dicyclohexylurea was filtered off and the residue was triturated with hexane) and was recrystallized from isopropanol/ether. Thin layer chromatography (TLC) was performed on Merck Alufolien and gave $R_f=0.56$ (n-BuOH:AcOH:$H_2O$, 4:1:1).

Example 3

Selecting an agent "X": A Procedure to Determine whether the (uncoupled) amine derivatizing agent "X" is significantly less soluble in a lipid bilayer compared to a derivatizing agent that is covalently coupled to a peptide of the invention

A. Introduction

This procedure is intended as a preliminary screening assay to identify amine derivatizing agents for coupling to the transport-mediating peptides to form the carrier molecules of the invention. A screening assay to identify carrier molecules for mediating transport of a membrane-impermeable exogenous agent is disclosed in Example 8.

Partitioning of a putative derivatizing agent into a lipid bilayer is determined using any of the following lipid vehicles: (1) unilammellar or multilammeller vesicles (liposomes) of known composition containing, for example, phosphatidyl choline (PC), phosphatidyl glyceride (PG) and phosphatidyl inositide (PI); micelles of lysophospholipids, PIP2 or PIP; and (3) mixed micelles of sodium dodecyl sulfate (SDS), triton and other phospholipids. Preferably, polyphosphoinositides (PPIs) are included in the lipid bilayer that is used for screening the putative derivatizing agents. A preferred method for forming vesicles of PIP and PIP2 is described below.

B. Phospholipids and Vesicle Preparation

Dioleoyl-L-alpha-phosphatidylcholine (PC), phosphatidylinositol 4-monophosphate (PIP), and phosphatidylinositol 4,5-bisphosphate (PIP2) were obtained from Sigma Chemical Corp., St. Louis, Mo. PIP and PIP2 were dissolved by sonication in water as described in Janmey and Stossel, J. Biol Chem. 264:4825-31 (1989)). Vesicles containing PC or PC and PIP2 at a 10:1 molar ratio were prepared by sonication. 1 mg of lyophilized PC was added to 0.1 mg of PIP2 in 1 ml of H20 and sonicated for 1 min at maximum power as previously described (Janmey and Stossel, J. Biol. Chem. 264:4825-31 (1989)).

Partitioning of the putative derivatizing agent into the lipid bilayer is determined without undue experimentation using any of the following methods. Selection of a particular type of detection method to determine the extent of partitioning is dependent upon the nature of the putative derivatizing agent. For example, for a putative derivatizing agent that is a fluorophore (fluorescent molecule), solubility of the derivatizing agent in the lipid bilayer is determined by observing the predicted changes in fluorescence spectra or intensity (quantum yield) that one of ordinary skill in the art would expect when the fluorophore partitions from an aqueous phase into a lipid phase. If the fluorophore is not environmentally-sensitive, partitioning into the lipid bilayer is detected by fluorescence quenching using acrylamide or similar molecules which reduce the fluorescence of the water soluble fluorophore. Such quenching reagents do not reduce the fluorescence of fluorophores bound in a lipid phase or partitioned within liposomes or micelles.

The partitioning into a lipid bilayer of non-fluorescent derivatizing agents that contain ester bonds or sulfhydryl groups is determined by observing changes in the susceptibility of such agents to esterases or reducing agents (e.g., Ellman's reagent or 7-dimethylamimo-4-methyl-(N-maleimidyl) coumarin (DACM) which changes fluorescence upon reacting with a sulfhydryl group). Ester bond or sulfhydryl group containing agents in an aqueous phase are susceptible to esterases or reducing agents. Such ester bond or sulfhydryl group containing agents are not susceptible to enzymatic cleavage or reducing agents when partitioned into a lipid bilayer.

The partitioning of radiolabeled derivizating agents into a lipid bilayer is determined by separating lipid particles from soluble components using, for example, ultracentrifugation, and measuring the relative proportions of radiolabel present in the lipid particle fraction compared with the soluble fraction.

Example 4

Non-Functional Procedures to Determine whether the carrier molecule (X-P) has been transported across the cell membrane:

A. Introduction

Non-functional procedures refers to tests which do not rely upon the functional activities of the derivatizing agent (X) or transport-mediating peptide (P) for detection. An exemplary method for determining whether the carrier molecule (X-P) has been transported across a cell membrane and into the intracellular matrix involves: (1) contacting a cell (e.g., HL60 or U937 cells grown in suspension) with a carrier molecule containing a labeled derivatizing agent (e.g., a fluorescent or radiolabeled derivatizing agent) and/or labeled transport-mediating peptides (e.g., radiolabeled peptides) for a time sufficient for the carrier molecule to enter the cell; (2) separating the cell from the soluble carrier molecule (e.g., by centrifugation, gel filtration chromatography); and (3) determining the relative proportions of the labeled carrier molecule in the cell fraction and the soluble fraction, e.g., by FACS (fluorescence activated cell sorting) for surface binding or incorporation. As a negative control, the same type of cells are contacted with the corresponding labeled, but unconjugated, derivatizing agent and/or transport-mediating peptide under identical conditions.

Transport of a carrier molecule into a cell also can be determined in an analogous manner to any of the methods disclosed in Example 3 for determining partitioning of the derivatizing agent into a lipid vehicle. Thus, for example, the partitioning of a carrier molecule which contains an ester bond or a sulfhydryl group into a cell can be determined by: (1) contacting the cell with the carrier molecule for a time sufficient for the carrier molecule to enter the cell; (2) separating the cell from the soluble carrier molecule which has not penetrated the cell (e.g., by centrifugation); and (3) determining the proportion of the carrier molecule present in the soluble fraction by exposing an aliquot of the soluble fraction to an esterase or reducing agent and determining the susceptibility of the soluble fraction to the esterase or reducing agent as a measure of the amount of carrier molecule present in the soluble fraction. Alternatively, the amount of carrier molecule remaining in the soluble fraction can be determined by an immunoassay (e.g., an ELISA assay employing antibodies to the carrier molecule or its components). In particular, biotin-containing carrier molecules present in the soluble fraction can be determined using streptavidin or avidin labeled with colloidal gold or a secondary antibody. See, e.g., Proc.Natl.Acad.Sci. U.S.A. 88:1864–1868 (1991) and WO 91/18981, published Dec. 12, 1991.

B. Gel Filtration Assay to Identify PPI-binding Peptides

This assay is similar to that described for studying PIP2 binding of profilin (Goldschmidt-Clermont P. J., et al., Science 251:1231–1233 (1991); Machesky. L. M., et al., Cell Reg.1:937–950 (1990)) and CapZ (Heiss and Cooper, Biochemistry 30:8753–8758 (1991)). It is based on the fact that PIP2 micelles are large (90 kDa) compared to the transport-mediating peptides of the invention (or carrier molecules containing these peptides), and polypeptide/PIP2 complexes will elute from a size exclusion gel filtration column earlier than the unbound polypeptide. The putative transport-mediating peptides (or carrier molecules containing these peptides) are incubated with PIP2 micelles for 5 min. at room temperature, and 100 ul of the mixture is chromatographed at room temperature on a Superose 12 HR 10/30 column (FPLC system, Pharmacia, Piscataway, N.J.) equilibrated with a buffer containing 5 mM Tris-HCl, pH 7.5, 75 mM KCl and 0.1 mM $NaN_3$. PIP2 is not included in the elution buffer. The elution is performed at 0.5 ml/min., and 0.5 ml fractions are collected. The elution profile is monitored by absorbance at 280 nm. 300 ul of selected fractions are dried down in a rotoevaporator (Speedvac), and analyzed by SDS-polyacrylamide gel electrophoresis. The amount of peptide bound to PIP is determined by measuring the decrease in the peptide absorbance peak. The sensitivity of this assay can be improved by using a labeled (e.g., radiolabeled) peptide and measuring the amount of label in the eluted fractions.

C. An Exemplary Protocol for Determining Transport of a Rhodamine-peptide conjugate into a Cell Mouse kidney fibroblasts (NIH3T3) were plated on a glass coverslip, allowed to spread and the coverslip was mounted on the stage of an inverted microscope equipped for epifluorescence. Rhodamine-SEQ. I.D. No. 2 conjugate was loaded into a micropipette at concentration of 10 μM in a buffer containing 154 mM NaCl, 10 mM Tris-HCl, pH 7.2. A marked group of cells were microinjected with the peptide conjugate and the intracellular localization was determined by viewing under fluorescent illumination. To determine if the peptide conjugate was transported across the cell membrane, a second group of cells was marked and the pipette tip placed near the cells. A small burst of peptide was ejected from the tip and allowed to briefly surround the cells, before being carried away by dilution. The cells were then viewed under fluorescent illumination to determine if they were now fluorescent. The intracellular location, as opposed to surface membrane adherence, was determined by comparing the localization of the peptide in each group of cells. The identical experiment can be repeated to assess the transport of a putative carrier into a cell by substituting the putative X-P carrier of the invention for the rhodamine-SEQ. I.D. No. 2 conjugate in the assay (using a broad concentration range, e.g., 0.01 μM to 1000 μM, of the putative carrier).

D. A Non-Functional Screening assay to determine whether an Exemplary X-P or X-P-A has associated with a membrane or hydrophobic layer Many fluorophores change emission spectra or intensities when bound to hydrophobic (lipid) ligands. Accordingly, the following assay is useful for determining whether an exemplary X-P or X-P-A has associated with a membrane or hydrophobic layer. We determined that the targets of an exemplary X-P are phosphoinositides (PPIs like PIP or PIP2) by adding increasing amounts of PPIs or control lipids to the exemplary X-P and measuring fluorescence changes to evaluate whether the X-P had bound to the hydrophobic ligand.

Figure 1B:
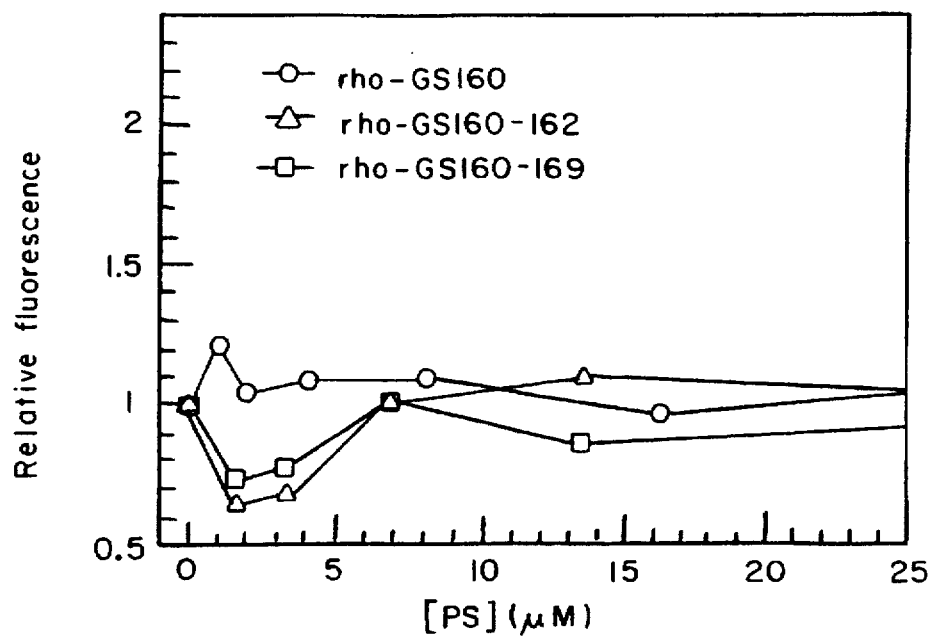
FIG. 1B shows that the lipid effect of FIG. 1A is specific for PIP2 since another acidic phopholipid PS (phophatidylserine) showed no effect on any of the tested rhodamine-peptide conjugates.

FIG. 1 shows the fluorescence intensity of 2 μM rhodamine-GS160-169 (i.e., rhodamine-SEQ. I.D. No. 2) as a function of the amount of PIP2 added to it in solutions containing 10 mM Tris pH 7.0. Very small amounts of PIP2 produced a large increase in rhodamine-GS160-169 fluorescence. In contrast, PIP2 did not perturb rhodamine-GS160, consistent with the lack of function of this peptide conjugate (i.e., rho-Gln) in cells. The fluorescence of the trimer peptide conjugate (rhodamine-GS160-162, i.e., rhodamine-QRL) was affected to a lesser extent by PIP2 than was rhodamine- GS160-169. This finding is consistent with the trimer peptide conjugate having less activity in cell assays. Figure 1B shows that the lipid effect was specific for PIP2 since another acidic phospholipid PS (phosphatidylserine) had no effect on any of the three peptides.

Example 5

Functional Procedures to Determine whether X-P has been transported across the cell membrane A. Introduction For carrier molecules which possess an intracellular activity, transport of the carrier molecule into a cell is determined by observing changes in, for example, cell morphology, following exposure of the cell to extracellular medium containing the carrier molecule. Negative controls include contacting the same type of cells with extracellular medium containing the (unconjugated) carrier molecule components, i.e., the derivatizing agent and the transport-mediating peptide. As a positive control, the carrier molecule can be introduced into the cell using conventional procedures (e.g., liposome delivery, microinjection). Each carrier molecule is tested over a wide concentration range to select the most effective carrier molecules for coupling to an exogenous agent to form a prodrug.

B. Determination of transport of the rhodamine-Seguence I.D. No. 2 conjugate into human melanoma cells Human melanoma cells, which typically exhibit surface instability by extending and retracting aneurysms (blebs), were exposed to micromolar quantities (2 µM) of the rhodamine-Sequence I.D. No. 2 conjugate in culture medium. Following exposure of the cells to the conjugate for 4 seconds, the melanoma cells flattened and stopped surface protrusion. As a positive control, a duplicate preparation of melanoma cells were microinjected with 2 µM (unlabeled) Sequence I.D. No. 2. The positive control cells exhibited the same morphological changes that were observed following exposure of the cells to the rhodamine-Sequence I.D. No.2 in the culture medium.

C. Determination of transport of the rhodamine-Sequence I.D. No. 2 conjugate into human blood platelets Coagulation of human or animal blood plasma by standard methods involving either recalcification of plasma or addition of thrombin causes formation of viscoelastic gels whose elastic strength (as measured by shear moduli) depends on the presence of intact platelets. Platelet rich plasma (PRP) or platelet poor plasma (PPP) were obtained from anticoagulated whole blood by centrifugation using standard methods. Using a standard commercial rheometer, the buildup of clot strength was measured (see Janmey et al. 1992 Blood) for samples with and without platelets or for PRP with or without X-P-A candidates.

Figure 2:
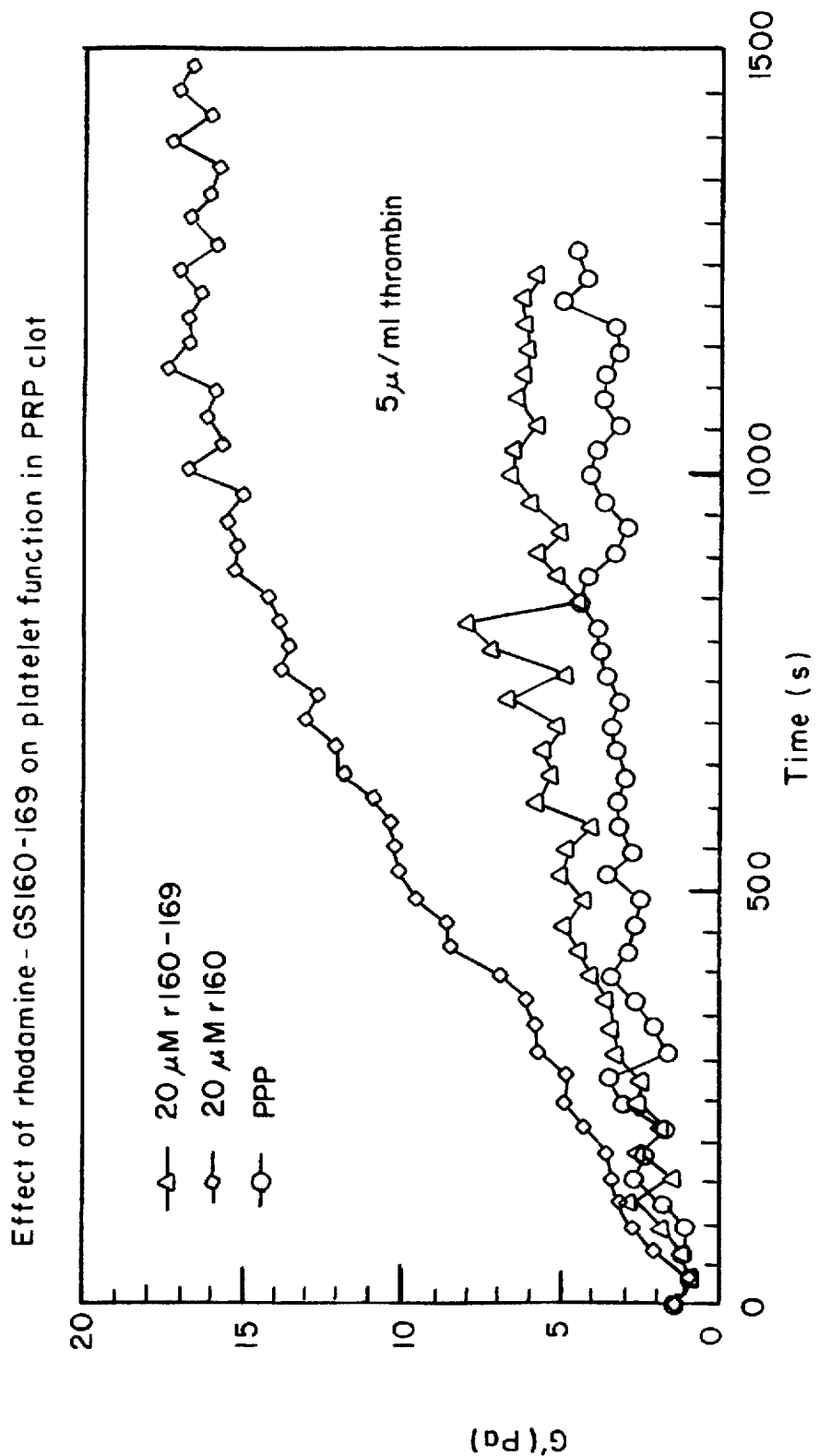
FIG. 2 shows the effect of rhodamine-SEQ. I.D. No. 2 on human blood platelet function, as determined by measuring the shear modulus of platelet rich plasma (PRP) during gel formation in the presence or absence of rhodamine-SEQ. I.D. No. 2.

As one example and demonstration of the specific effect of Rho-GS160-169 on human platelet function, FIG. 2 shows the shear modulus of PRP during gel formation with or without rhodamine-GS160-169. The figure shows that addition of 20 µM rhodamine-GS160-169 to PRP produced a clot with the same relatively low shear modulus as a PPP clot, whereas addition of rhodamine-GS160 does not alter platelet function, and therefore, the clots formed in its presence were several times stronger (i.e., have a higher shear modulus G').

D. Determination of transport of an X-P into a cell based upon changes in cell motility Contacting a cell with the X-P carrier molecule should result in peptide-mediated inhibition of PIP2 hydrolysis and therefore cell locomotion. Two assays can be used to measure changes in cell locomotion. The first assay employs a two compartment Boyden chamber. Migration through a membrane in response to a chemoattractant is assayed using a 48-well chamber (Nucleopore, Pleasanton, Calif.) with a 5 µm polycarbonate filter. Cells (either fibroblasts, melanoma cells or neutrophils) are trypsinized, counted, and $5 \times 10^4$ cells per well are loaded in the top wells. The bottom wells are loaded with media with or without a chemoattractant so that the cells are exposed to either a gradient, reverse gradient, or no gradient of attractant media. The chambers are incubated for 2 hours at 37° C., the membranes removed, stained and then examined with a Zeiss Axiovert microscope with a 40× objective. The number of cells that migrate through the membrane are counted for each well and indicate the motile ability of the cells. To assay for X-P transport, a portion of the cells are first incubated in X-P at the concentration required for transport as determined above, then loaded on the chamber. The effects on motility are indicated by a reduced number of cells migrating through the membrane.

Alternatively, wound healing assays can be used to measure cell motility. A dish of confluent cells is scored with the tip of a rubber policeman. The width of the wound is measured by observation through an Olympus CK inverted tissue culture microscope with a grid reticule in the eyepiece. This allows measurement of the width of the wound when first made and at intervals thereafter, as the migrating cell edges close the wound. Care is taken to measure the wound in the same locations at each interval. The rate of closure of the wound edge reflects the locomotory rate of the cells along the edge. This assay can be performed in the presence or absence of the peptide to determine the effects on motility, and therefore of peptide transport into the cells.

Example 6

Selecting an agent "A": A Procedure to Determine whether the (uncoupled) agent is membrane-impermeable, e.g., by determining solubility of "A" (coupled vs. uncoupled forms) in a lipid bilayer Introduction This procedure is intended as a preliminary screening assay to identify membrane-impermeable exogenous agents for coupling to the carrier molecules to form the prodrugs of the indeteron. Membrane-impermeability is determined by comparing the solubilities of an unconjugated and a conjugated putative membrane-impermeable exogenous agent in a lipid bilayer or other hydrophobic layer. As used herein, "membrane-impermeable" in reference to an exogenous agent means an exogenous agent which cannot penetrate the cell membrane at a sufficient level to mediate its intracellular function.

Partitioning of the exogenous agent into a lipid bilayer is determined using any of the following lipid vehicles: (1) unilammellar or multilammeller vesicles (liposomes) of known composition containing, for example, phosphatidyl choline (PC), phosphatidyl glyceride (PG) and phosphatidyl inositide (PI); micelles of lysophospholipids, PIP2 or PIP; and (3) mixed micelles of sodium dodecyl sulfate (SDS), triton and other phospholipids. Preferably, polyphosphoinositides (PPIs) are included in the lipid bilayer that is used to evaluate partitioning of the exogenous agent into a lipid bilayer. The preferred method for forming vesicles of PIP and PIP2 is described above (Example 3).

Partitioning of the exogenous agent into the lipid bilayer is determined without undue experimentation using any of the following methods. Selection of a particular type of detection method to determine the extent of partitioning is dependent upon the nature of the exogenous agent. For example, for an exogenous agent that is labeled with a fluorescent molecule, solubility in the lipid bilayer is determined by observing the predicted changes in fluorescence spectra or intensity (quantum yield) that one of ordinary skill in the art would expect when the fluorophore partitions from an aqueous phase into a lipid phase. Other methods for determining the extent of extracellular agent partitioning into a lipid bilayer are as described above for determining partitioning of a putative derivatizing agent into a lipid bilayer, with the exception that the exogenous agent is substituted for the derivatizing agent in the above-described protocols.

Example 7

Procedure for Synthesizing X-P-A

Depending upon the nature of the reactive groups of the derivatizing agent, the transport-mediating peptide and the extracellular agent, the prodrug (X-P-A) is formed by simultaneously or sequentially allowing the functional groups of the above-described components to react with one another. In a preferred embodiment in which the extracellular agent is a peptide, the prodrug is formed by coupling the derivatizing agent to the N-terminal amino acid of the transport mediating peptide and sequentially adding the amino acids of the transport-mediating peptide until a carrier molecule having the formula X-P is formed. Thereafter, the N-terminal amino acid of the extracellular agent can be coupled to the C-terminal of the carrier molecule and the remaining amino acids of the extracellular peptide can be added sequentially until the complete prodrug is formed. In the preferred embodiments, the prodrug is formed by allowing the transport-mediating peptide to first react with the derivatizing agent to form the carrier molecule X-P, and then allowing the carrier molecule to react with the extracellular agent A to form the prodrug X-P-A. For extracellular agents that are peptides/proteins, the transport-mediating peptide/extracellular agent complex alternatively can first be synthesized on a solid support using standard peptide synthesis chemistries and then covalently attached to the derivatizing agent.

An angiotensin prodrug is formed using a solid phase synthesis method in which the peptide chain is step-wise elongated as described above. Appropriate spacer molecules (e.g., episilon-amino-capronic acid "Fmoc-Aca") optionally is introduced between the transport-mediating peptide and the extracellular agent. Various other linkers (spacer molecules) can be used to insert molecules of known composition and size between any of the derivatizing agent, the transport-mediating peptide and the extracellular agent. Such agents are commercially available (see, e.g., Sigma Chemical Co. catalog, St. Louis, Mo. (1992)).

An exemplary procedure for forming a nucleoside prodrug is described herein. 2', 3', O-isopropylidene-inosine (Sigma, St. Louis, Mo., product I-4502) is acylated with Fmoc-Aca using the chloroanhydride method. The isopropylidene group is removed by treating the product of the foregoing reaction with trifluroacetic acid. Other nucleosides, nucleotides, or oligonucleotides are substituted for 2', 3', O-isopropylidene-inosine to form the corresponding nucleoside, nucleotide or oligonucleotide prodrugs.

Antibiotic prodrugs which have a free hydroxyl group are prepared using Fmoc-Aca to derivatize the antibiotic and thereafter couple the derivatized antibiotic to a carrier molecule of the invention. Antibiotics which already include a reactive functional group, for example, ampicillin (Sigma, St. Louis, Mo., product A-9393) are directly attached to the carrier molecule or can be coupled via a spacer molecule if so desired using the above-described chemistries.

Example 8

Non-Functional Procedures to Determine whether X-P-A has been transported across the cell membrane Non-functional procedures refers to tests which do not rely upon the functional activity of the exogenous agent for detection, for example, the exogenous agent contains a detectable label such as a fluorescent molecule. As a control, the cells are contacted with labeled exogenous agent which is not covalently coupled to the carrier molecule. In general, the screening method is performed in an identical fashion to the non-functional procedures described above for determining whether the carrier molecule has been transported across a cell membrane (Example 4), with one exception being that the detectable label is present on the exogenous agent. Other changes to Example 4 include that in addition to looking at intracellular fluorescence, the cells are permeabilized and incubated with a biotin or peroxidase-labelled antibody to the extracellular agent (A). Specific binding of the antibody is detected by calorimetric development of the label after extensive washing of the cells in PBS. The presence of the antibody within the cells indicates that the extracellular agent A was carried across the cell membrane.

Example 9

Functional Procedures to Determine whether X-P-A has been transported across the cell membrane Certain strains of bacteria are able to invade mammalian cells and replicate intracellularly (reviewed by Moulder, J. W. (1985) *Microbiol Rev* 49:298–337). One advantage which accrues to the bacteria as a result of this is protection from antibodies which do not cross the cell membrane. This phenomena then provides a functional assay for measuring the ability of an exemplary X-P-A to cross the cell membrane in cases where A is one of a broad spectrum of antibiotics.

Strains of bacteria that are known to invade mammalian cells (e.g., Listeria, Salmonella) are cultured in Luria broth (LB). To assay, $1\times10^7$ bacteria are added to $1\times10^6$ adherent cells cultured in 24-well microtiter plates without antibiotics. After a 2 hour incubation at 37° C., 5% $CO_2$, the monolayers are washed 3× with phosphate-buffered saline (PBS) and extracellular bacteria are killed by the addition of fresh tissue culture media to which 100 µg/ml gentamycin is added. Efficient bacterial killing requires a further 2 hour incubation at 37° C., 5% $CO_2$. The monolayers are then washed 3× with PBS, lysed with 0.1 ml 1% Triton X-100, and the number of viable internal bacteria are determined by titration of the cell lysate on LB agar with 100 µg/ml ampicillin.

To test X-P-A, a concentration of the compound sufficient to achieve intracellular levels of antibiotic equal to the measured MIC (minimal inhibitory concentration) of the antibiotic is added (with the extracellular gentamycin) to the monolayer. The number of viable intracellular bacteria is measured in the presence or absence of X-P-A. X-P (without A) serves as an additional negative control. Other concentrations of X-P-A are tested to confirm that the MIC is significantly less if the antibiotic is delivered intracellularly.

Example 10

Protocol for Modulating Bacterial Contamination in Cell Culture

Most bacterial contaminations in cell cultures are from extracellular bacteria. The one noted exception is Mycoplasma species, which are intracellular. A procedure for modulating Mycoplasma contamination is presented below.

Between 5–35% of current cell cultures are estimated to be infected with mycoplasma species (McGarrity, G. (1982) *Adv Cell Culture* 2:99–131). Several antibiotics are effective against such infections but require extended treatment of the culture (Drexler, H. G., S. M. Gignac et al. (1994) "Treatment of mycoplasma contamination in a large panel of cell cultures" *In Vitro Cell Dev Biol Anim*, 344–377). Treatment time is significantly reduced by increasing the intracellular level of antibiotic. Accordingly, X-P-A is synthesized as described in Example 7, with "A" in this instance being an antibiotic such as ciprofloxacin. The results of the functional assay in Example 5 are used to determine an effective intracellular MIC and that concentration of X-P-A is incubated with the cells for 2 to 24 hours to determine the effect of incubation time with X-P-A on Mycoplasma contamination.

Example 11

Protocol for In situ hybridization using an X-P-oligonucleotide

An oligonucleotide probe having a nucleotide sequence complementary to, for example, a nucleic acid sequence encoding a viral-specific protein, is prepared according to standard procedures. For example, the target nucleic acid can contain a sequence encoding a unique protein product of the HIV virus. The oligonucleotide is covalently coupled to rhodamine-SEQ. I.D. No.2, according to the protocol presented above in Example 7 to form an "oligonucleotide prodrug".

The cells which are intended for in situ hybridization analysis are prepared according to standard procedures. The cells may be fixed on unfixed prior to contacting the cells with the oligonucleotide prodrug.

The oligonucleotide prodrug is incubated in the presence of cells which are being tested for the presence of a target nucleic acid for a time sufficient for the oligonucleotide prodrug to be transported across the cell membrane. Routine optimization of transport conditions such as time, temperature, concentration, are performed according to standard practice.

The oligonucleotide prodrug facilitates transport of the oligonucleotide probe or primer that is complementary to a target nucleic acid across the cell membrane, thereby facilitating in situ hybridization of the probe or primer to intracellular target nucleic acid. In situ hybridization is performed and the results are analyzed according to standard procedures (see, e.g., Molecular Cloning, 2nd edition, ed. Sambrook et al., Cold Spring Harbor Laboratory Press (1989)).

Example 12

Protocol for Using X-P-imaging agent for Diagnosis of a Medical Condition

Exemplary imaging agents that are attached to a carrier molecule include those identified in U.S. Pat. No. 4,861,581, issued to Epstein et al. These include (1) radiolabels; (2) radiopaque materials; and (3) magnetic resonance enhancing materials. Exemplary radiolabels include: Tc-99m, I-123, I-125, In-111, In-113m, Ga-67, or other suitable gamma-emitters. Exemplary radiopaque materials include iodine compounds, barium compounds, gallium compounds, thallium compounds, and the like. Specific examples of radiopaque materials include: barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosumetic acid, iotasul, iotetric acid, iothalamic acid, iotroxic acid, ioxaglic acid, ioxotrizoic acid, opodate, meglumine, metrizamide, metrizoate, propyliodone, and thallous chloride. Magnetic resonance enhancing materials refer to materials that can be detected by or that enhance the effects of magnetic resonance imaging equipment. Exemplary magnetic resonance enhancing materials include gadolinium, copper, iron, and chromium. It is preferred that these metal atoms be prepared in the form of a conventional organometallic chelates, which are then bound to the carrier.

The above-identified imaging agents are coupled to the carrier molecule (X-P) using conjugation procedures known to those of ordinary skill in the art. Exemplary procedures are described in U.S. Pat. No. 4,861,581.

Example 13

Protocol for Using X-P-therapeutic agent for Treatment of a Medical Condition

Exemplary therapeutic agents are disclosed above. Such agents are conjugated to a carrier using conjugation reactions that are known to those of ordinary skill in the art (see, e.g., U.S. Pat. No. 4,861,581 and Example 3, above). As would be apparent to one of ordinary skill in the art, the exact dose of prodrug to be given to an individual is determined by consideration of the nature of the condition being treated, whether the condition is acute or chronic, the biological characteristics of the individual being treated (e.g., body weight, size and general health characteristics). In general, dosages are determined in accordance with standard practice for optimizing the correct dosage for treating the medical disorder, i.e., improving the condition and/or delaying progression of a disease or disorder. The therapeutic agent prodrug is administered according to standard practice. For example, topical formulations of the prodrug are formulated in an ointment or cream for surface administration. Exemplary prodrugs for topical application include antisense prodrugs which are directed to inhibiting transcription of viruses such as those associated with, for example, genital herpes. Such topical formulations further can include chemical compounds such as dimethylsulfoxide (DMSO) to faciliate surface penetration of the active ingredient, e.g., the antisense prodrug.

The methods and compositions of the invention are also useful for delivering a therapeutic agent such as an antibiotic that is normally unable to cross the cell membrane but that is highly active against an intracellular pathogen (Tulkens 1990; Tulkens 1991; van, den et al. 1991; Van, der et al. 1991). Typically, such antibiotic prodrugs are administered intravenously.

Each reference identified above is incorporated herein in its entirety by reference. It should be understood that the preceding is merely a detailed description of certain preferred embodiments. It therefore should be apparent to those skilled in the art that various modifications and equivalents can be made without departing from the spirit or scope of the invention. Accordingly, it would be apparent to one or ordinary skill in the art that the various fragments, homologs and analogs of the invention can be contained within a larger peptide-mediating peptide without departing from the essence of the invention disclosed herein.

A Sequence Listing is presented below and is immediately followed by what is claimed.

We claim:

1. A molecule having the formula X-P, wherein (a) P is a peptide selected from the group consisting of Seq. I.D. No. 1 and Seq. I.D. No. 2; and (b) X is rhodamine or a rhodamine derivative, wherein X is covalently coupled to the N-terminus amine of the peptide.

2. The molecule of claim 1, wherein X is rhodamine.

3. The molecule of claim 1, wherein P is Seq. I.D. No. 2.

4. The molecule of claim 2, wherein P is Seq. I.D. No. 2.

5. A molecule having the formula X-P, wherein (a) P is a peptide fragment of a peptide selected from the group consisting of Seq. I.D. No. 1 and Seq. I.D. No. 2, wherein the peptide fragment is a basic polyphosphoinositide binding peptide and contains between three and ten amino acids; and (b) X is rhodamine or a rhodamine derivative, wherein X is covalently coupled to the N-terminus amine of the peptide fragment.

6. The molecule of claim 5, wherein X is rhodamine.

7. The molecule of claim 5, wherein the peptide fragment is a peptide fragment of Seq. I.D. No. 1.

8. The molecule of claim 5, wherein the peptide fragment is a peptide fragment of Seq. I.D. No. 2.

9. The molecule of claim 8, wherein the peptide fragment of Seq. I.D. No. 2 is selected from the group consisting of Seq. I.D. Nos. 8, 9, 10, 11, 12, 13, 30, 31, 32, 33, 34, 35 and 36.

10. A molecule having the formula X-P, wherein
(a) P is a peptide that is a polyphosphoinositide binding peptide consisting essentially of between 3 and 10 amino acids of a polyphosphoinositide domain of a polyphosphoinositide binding protein; and
(b) X is rhodamine or a rhodamine derivative, wherein X is covalently coupled to the N-terminus amine of the peptide.

11. The molecule of claim 10, wherein X is rhodamine.

12. The molecule of claim 10, wherein P is selected from the group consisting of Seq. I.D. Nos. 14, 15, 16, 17, 18, 19, 20, 21, 22, and 23.

13. The molecule of claim 11, wherein P is selected from the group consisting of Seq. I.D. Nos. 14, 15, 16, 17, 18, 19, 20, 21, 22, and 23.

* * * * *

UNITED STATES PATENT AND TRADEMARK OFFICE

CERTIFICATE OF CORRECTION

PATENT NO. : 5,783,662
DATED      : July 21, 1998
INVENTOR(S): Paul A. Janmey et al.

It is certified that error appears in the above-identified patent and that said Letters Patent is hereby corrected as shown below:

Col. 1, line 5, in the "Government Support" section, at the word "Health.", please delete "." and add --including numbers HL47874, HL19429, AR38910 and R03 TW00100.--

Signed and Sealed this

Fourteenth Day of December, 1999

Attest:

Q. TODD DICKINSON

Attesting Officer

Acting Commissioner of Patents and Trademarks